United States Patent [19]

Tomoda et al.

[11] Patent Number: 5,296,607
[45] Date of Patent: Mar. 22, 1994

[54] PHOTOCHROMIC COMPOUND

[75] Inventors: Akihiko Tomoda; Hisao Suzuki; Akira Kaneko; Hideki Tsuboi, all of Hamamatsu, Japan

[73] Assignee: Yamaha Corporation, Hamamatsu, Japan

[21] Appl. No.: 902,778

[22] Filed: Jun. 23, 1992

Related U.S. Application Data

[63] Continuation of Ser. No. 607,999, Oct. 31, 1990, abandoned.

[30] Foreign Application Priority Data

Nov. 8, 1989 [JP] Japan .................... 2-90578
Jul. 18, 1990 [JP] Japan .................... 1-89664

[51] Int. Cl.⁵ ............................. C07D 413/06
[52] U.S. Cl. ........................ 548/236; 548/469; 548/546; 548/547; 549/60; 549/252
[58] Field of Search .......... 549/252, 60; 548/469, 548/546, 547

[56] References Cited

U.S. PATENT DOCUMENTS 4,220,708 9/1980 Heller .................... 548/236
4,845,240 7/1989 Hibino .................... 549/252

FOREIGN PATENT DOCUMENTS

60-52150 11/1985 Japan .
63-166879 7/1988 Japan .................... 548/374
1-034983 2/1989 Japan .................... 548/200

Primary Examiner—Robert Gerstl
Attorney, Agent, or Firm—Spensley Horn Jubas & Lubitz

[57] ABSTRACT

In chemical structure of a fulgide type photochromic compound having the following general formula;

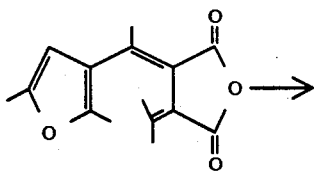

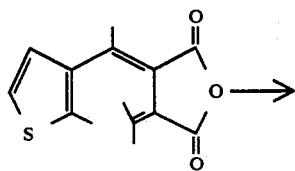

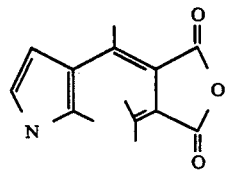

introduction of electron donative groups into its heteroaromatic structure is effective in improving the long wave length sensitivity without any lowering in its thermal stability. Thanks to such combined functional properties, the products are advantageously used for optical recording media, copying media, printing media, optical filters and display materials.

1 Claim, 6 Drawing Sheets

PHOTOCHROMIC COMPOUND

This is a continuation of application Ser. No. 607,999, filed on Oct. 31, 1990, now abandoned.

BACKGROUND OF THE INVENTION

The present invention relates to a photochromic compound, and more particularly relates to a fulgide type photochromic compound advantageously used for optical recording and copying media.

Fulgide compounds are widely known as one of typical photochromic compounds as disclosed, for example, in Japanese patent publication Sho. 60-52150 and U.S. Pat. No. 4,220,708. In chemical structure of a fulgide compound, two methylenecarbons of succinic anhydride or its derivatives are each accompanied with an alkylidene group. When irradiated with a light of a constant wave length, a fulgide compound exhibits change in chemical structure and, on irradiation with a light of a particular wave length, resumes its initial chemical structure.

Utilizing such a photochemical property, fulgide compounds are generally used for optical recording and copying media. When used for such applications, a photochromic compound is required to have the following functional properties.

(i) High durability against repeated use, i.e. possibility in repeated recording and erasing of information.

(ii) Good thermal stability in darkness, i.e. reliable maintenance of colored and uncolored form.

(iii) High long wave length sensitivity, i.e. fitness to semiconductor lasers.

(iv) Non-destructive reading.

It is reported by H. G. Heller that a photochromic compound having high long wave length sensitivity can be obtained by changing the heteroaromatic structure of a fulgide compound from furan via thiophen to pyrrole as follows;

This change in heteroaromatic structure makes the maximum absorption wave length rise up to 600 nm. Despite this merit, high aromatic character of the pyrrole tends to degrade thermal stability of the colored form of the compound [see A. Kaneko et al, Bull, Chem, Soc, Jpn., 3569 (1988)].

For effective use of a photochromic compound, the compound is required to suffice the above-described three functions (i) to (iii) together. Change in heteroaromatic structure proposed by Heller cannot assure provision of such an excellent photochromic compound.

SUMMARY OF THE INVENTION

It is the object of the present invention to provide a photochromic compound having high thermal stability with high long wave length sensitivity.

In accordance with the present invention, a photochromic compound characterized by a general formula in which said $R_1$ to $R_4$ in said formula indicate hydrogen, an alkyl group or an aryl group, said X in said formula indicates oxygen or N-$R_6$, $R_6$ indicating hydrogen, an alkyl group, an aryl group or an allyl group, said ring A is given in the form of one of the following six chemical groups [(II) to (VII)];

in said chemical groups (II) to (IV), $R_5$ and $R_7$ are electron donative groups and each given in the form of an alkyl group, an alkoxyl group, an amino group, a di-alkyl amino group, a mono-alkyl amino group, a pyrrolyl group, a indolyl group, a compound as shown in (VIII)

(VIII)

(in which said $R_{10}$ indicates an alkoxyl group, an amino group, a di-alkyl amino group or a mono-alkyl amino group; and l and m indicate integers from 0 to 5), a compound as shown in (IX)

(IX)

(in which said $R_8$ indicates an alkyl group, an aryl group, an aralkyl group or an allyl group; said ring B indicates a 5 or 6 membered heteroaromatic ring or a condensed ring containing a 5 or 6 membered heteroaromatic ring; and n indicates an integer from 0 to 4), and in said chemical groups (V) to (VII), $R_5$ is given in the form of an alkyl group, an amino group, a di-alkyl amino group, a mono-alkyl amino group, a pyrrolyl group, an indolyl group, a compound as shown in (X)

(X)

(in which said $R_{10}$ indicates an alkoxyl group, an amino group, a di-alkyl amino group, or a mono-alkyl amino group, l indicates an integer from 0 to 5; and m indicates an integer from 1 to 5), or a compound as shown in (XI)

(XI)

(in which said $R_8$ indicates an alkyl group, an aryl group, an aralkyl group, or an allyl group; said ring B indicates a 5 or 6 membered heteroaromatic ring or a condensed ring containing a 5 or 6 membered heteroaromatic ring; and n indicates an integer from 0 to 4), and in said chemical groups (V) and (VI), K is 1 or 2, and in said chemical group (VII), k is an integer from 1 to 4; and z indicates O, S, N-$R_9$ (in which $R_9$ indicates an alkyl group, an aryl group, an aralkyl group or an allyl group).

DESCRIPTION OF THE PREFERRED EMBODIMENTS

Figure 1:
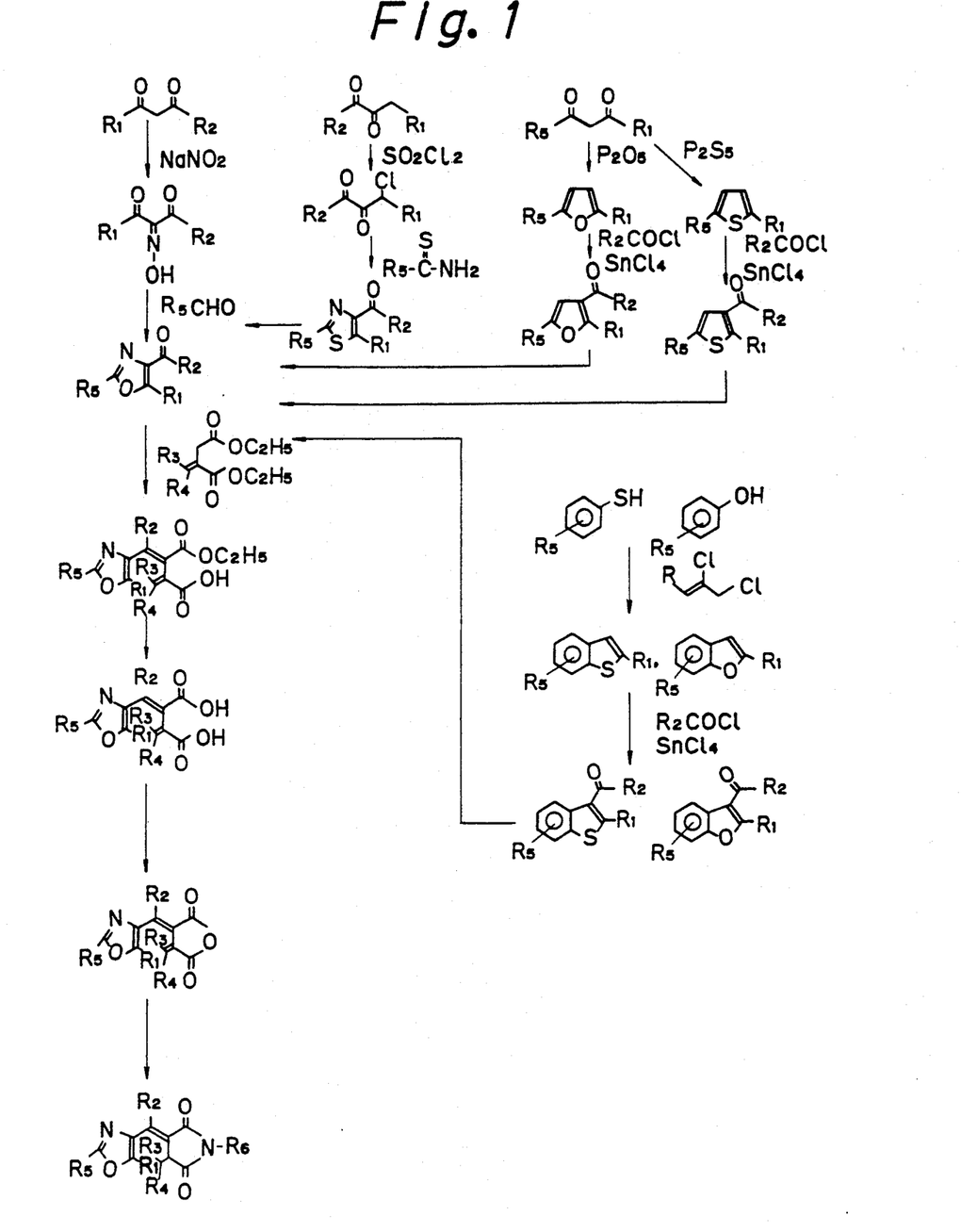
FIG. 1 is an explanatory scheme for showing one example of synthesis of the photochromic compound in accordance with the present invention.

The photochromic compound in accordance with this invention is synthesized, as shown in FIG. 1, from pentadione derivatives into oxazole derivatives, thiazole derivatives, furan derivatives and thiophen derivatives, respectively. This synthesis is followed by Stobbe condensation with succinic di-ester.

Thanks to introduction of electron donative groups into the heteroaromatic structure, the fulgide compound of the above-described general formula is much improved in its long-wave length sensitivity without lowering its thermal stability, i.e. maintenance of colored and uncolored form.

The fulgide compound of this invention exhibits clear photochromism. That is, irradiation with ultraviolet beam changes its non-coloured open form into a coloured closed form and irradiation with visible light changes the closed form back into the initial non-coloured open form as shown below.

Thanks to such functional properties, the photochromic compound of the present invention is advantageously used for optical recording media, copying media, printing media, optical filters and display materials.

DESCRIPTION OF EXAMPLES

EXAMPLE 1

Synthesis of (E)-α-5-methyl-2-phenyl-4-oxazolyl ethylidene (isopropylidene) succinic anhydride.

(1) Synthesis of 4-acetyl-5-methyl-2-phenyloxazole.

300 g of acetylacetone was dissolved in 500 ml of glacial acetic acid and 250 g of sodium nitrite was dissolved in 500 ml of water. While stirring the first solution, the second solution was added by dropping.

The reaction product was extracted with diethyl ether and, after removal of the solvent, 169 g of hydroxyimino acetylacetone was obtained by recrystalization from toluene (melting point; 74° to 87° C.).

Next, 100 g of hydroxyimino acetylacetone and 82 g of benzaldehyde were dissolved in 240 ml of glacial acetic acid. The solution was kept at 0° to 5° C. and subjected to flow of hydrogen chloride gas for 4 hours.

1.5 l of diethylether was added to the solution to separate precipitation and recrystalization was carried out by addition of acetone to produce 129 g of 4-acetyl-5-methyl-2-phenyloxazole N-oxide hydrochloride (melting point; 85° to 87° C.)

Next, 100 g of 4-acetyl-5-methyl-2-phenyloxazole N-oxide hydrochloride was dissolved in 500 ml of glacial acetic acid and 100 g of zinc powder was added to the solution while cool stirring within a ice water bath. The separation was filtered after addition of 2 l of water and recrystalization was carried out by addition of methanol to produce 10 g of 4-acetyl-5-methyl-2-phenyloxazole (melting point; 74° to 76° C.).

(2) Synthesis of the fulgide compound (II)

100 g of potassium-t-butoxide was dissolved in 800 ml of butanol, and a mixture of 174 g of diethyl succinate and 46.5 g of acetone was added to this solution which was then heated for 30 min. After extraction with diethyl ether, the obtained half ester was added to a mixture of 1 l of ethanol with 10 ml of concentrated sulfuric acid and the new mixture was refluxed for 8 hours. After removal of the solvent and extraction with diethyl ether, 120 g of diethyl isopropylidene succinate (boiling point; 74° to 75° C./2 mmHg) was obtained via low pressure distillation.

Next 3.6 g of potassium-t-butoxide was dissolved in 40 ml of butanol and a mixture of 5.8 g of 4-acetyl-5-methyl-2-phenyloxazole with 7.7 g of diethyl isopropylidene succinate was added to the solution which was then refluxed. After removal of solvent, 200 ml of 5 W/V sodium hydroxide-ethanol solution was added and the mixture was heated and refluxed for 11 hours. Obtained precipitation by addition of hydrochloric acid was extracted with ethyl acetate and, after removal of solvent, the residue was dissolved in 50 ml of acetic anhydride. Heating followed at 90° C. for 30 min. Via recrystalization from hexan/chloroform, 1.4 g of (z)-α-5-methyl-2-phenyl-4-oxazolyl ethylidene (isopropylidene) succinic anhydride was obtained (melting point; 131° to 132.5° C.).

Next, 100 mg of (z)-α-5-methyl-2-phenyl-4-oxazolyl ethylidene (isopropylidene) succinic anhydride was dissolved in 1 l of benzene and the solution was subjected to light radiation for 3 hours. After removal of solvent, recrystalization from hexan/chloroform produced 20 mg of (E)-α-5-methyl-2-phenyl-4-oxazolyl ethylidene (isopropylidene) succinic anhydride (melting point; 157° to 160° C.).

The result of measurement of this fulgide compound is shown in Table 1.

TEST 1

The fulgide compound obtained in the foregoing Example 1 was dissolved in toluene to produce a $1 \times 10^{-4}$ mol/l solution. This solution was subjected to radiation with ultraviolet beam of 365 nm wave length for 60 seconds using a glass filter (produced by TOSHIBA GARASU; UV-35+UV-D36C) and a 300 W high pressure Hg lamp (produced by USHIO DENKI). The solution was colored and the fulgide compound was changed into a closed form showing its maximum absorption at 462 nm wave length.

Subsequent irradiation was carried out for 40 seconds with visible light of 390 nm or longer wave length using a 300 W xenon lamp (produced by USHIO DENKI) and a glass filter (produced by TOSHIBA GARASU; L-39). Then the solution was discoloured and changed into the initial open form showing its maximum absorption at 339 nm wave length.

Figure 2:
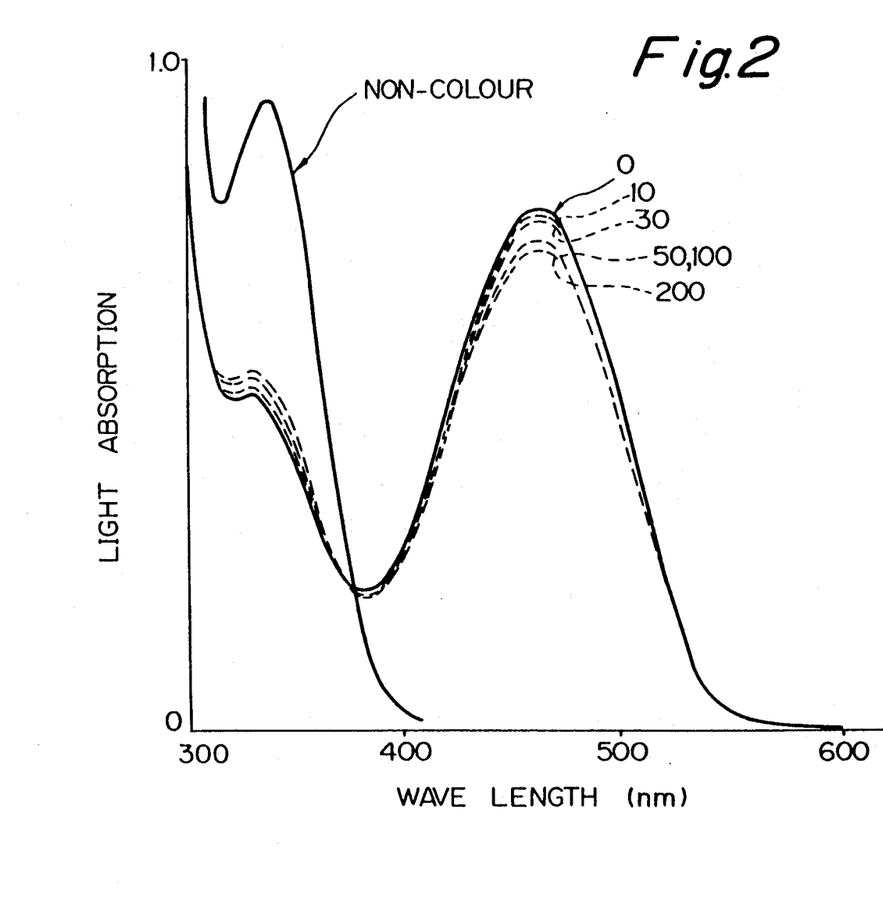
FIG. 2 is absorption spectrums of the open and closed form of the photochromic compound in Example 1.

Alternate irradiation was carried out for 200 times with ultraviolet beam of 365 nm wave length and visible light of 390 nm or longer wave length and change in absorption spectrum was measured. The result of the measurement is shown in FIG. 2 in which figures attached to the curves indicate the number of repetition in colouration and discolouration.

EXAMPLE 2

Synthesis of (z)-α-5-methyl-2-p-dimethyl amino phenyl-4-oxazolyl ethylidene (isopropylidene) succinic anhydrid.

As a substitute for the middle product in Example 1, i.e. 4-acetyl-5-methyl-2-phenyl oxazole, 4-acetyl-5-methyl-2-p-dimethyl amino phenyl oxazole was used under other conditions same as those in Example 1 to produce 0.7 g of the above-described fulgide compound (melting point; 202° to 204° C.). The result of measurement applied to this compound is shown in Table 2.

TEST 2

Figure 3:
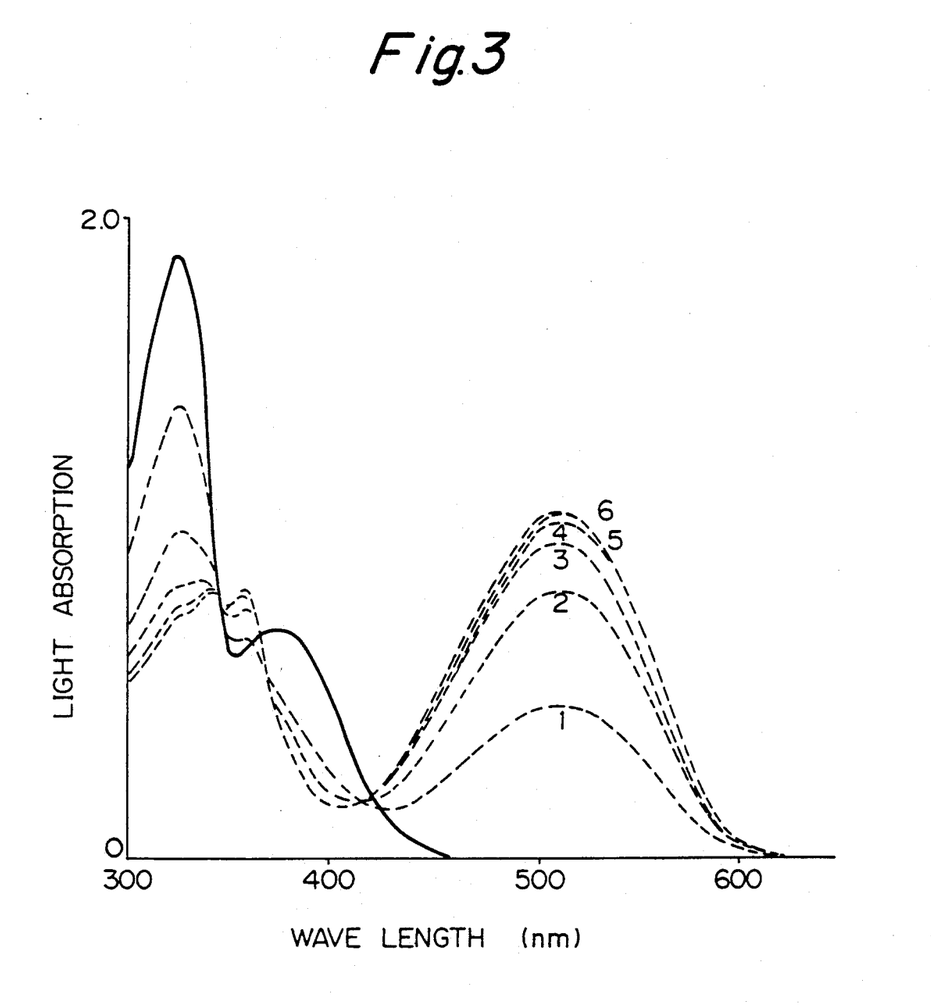
FIG. 3 is absorption spectrum changes for the photochromism of the photochromic compound in Example 2.

The fulgide compound obtained in Example 2 was dissolved in toluene to produce a $0.7 \times 10^{-4}$ mol/l solution. This solution was subjected to radiation with a light of 405 nm wave length for 6 min using a 250 W high pressure Hg lamp (produced by USHIO DENKI) and a glass filter (produced by TOSHIBA GARASU; L-39+KL-40). The solution was coloured and changed into a closed form showing its maximum absorption at 510 nm wave length. This absorption spectrum change is shown in FIG. 3 in which figures indicate irradiation time in min.

Thereafter, the colored solution was subjected to radiation with visible light of 500 nm or longer wave length for 3 min. The solution returned to the initial open form of E isomer. This change could be repeated more than 500 times.

EXAMPLE 3

Synthesis of (z)-α-5-methyl-2-p-dimethylamino styryl-4-oxazolyl ethylidene (isopropylidene) succinic anhydride.

As a substitute of the middle product in Example 1, i.e. 4-acetyl-5-methyl-2-phenyl oxazole, 4-acetyl-5-methyl-2-p-dimethylamino styryl-4-oxazole was used under conditions same as those in Example 1 to produce the above-described fulgide compound (melting point; 209° to 210° C.). The result of measurement applied to this compound is shown in Table 3.

TEST 3

Figure 4:
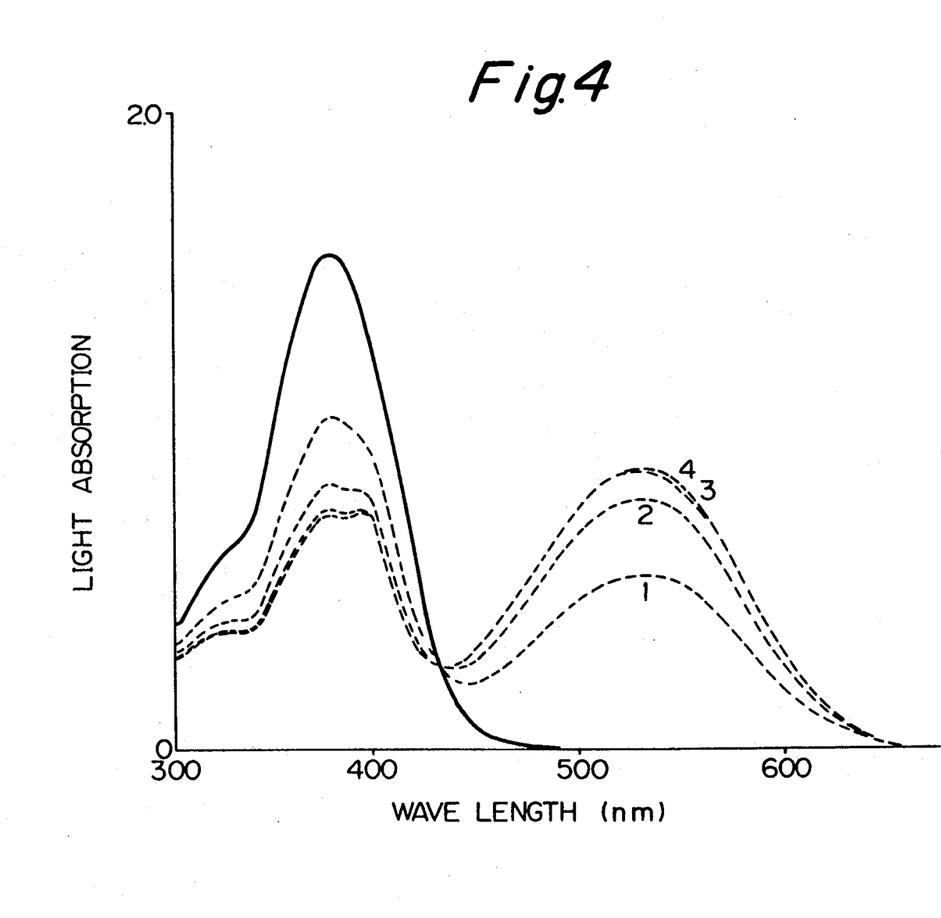
FIG. 4 is absorption spectrum changes for the photochromism of the photochromic compound in Example 3.

Absorption spectrum measurement was carried out using the fulgide compound obtained in Example 3 under conditions same as those in Test 2. The result is shown in FIG. 4 in which figures indicate irradiation time in min.

EXAMPLE 4

Synthesis of (E)-α-2-methyl-5-p-diethylamino styryl-3-thenylidene (isopropylidene) succinic anhydride.

As a substitute for the middle product in Example 1, i.e. 4-acetyl-5-methyl-2-phenyl oxazole, 5-p-diethylamino styryl-3-formyl-2-methylthiophene was used under conditions same as those in Example 1 to produce the above-described fulgide compound (melting point; 168° to 172° C.). The result of measurement is shown in Table 4.

TEST 4

Figure 5:
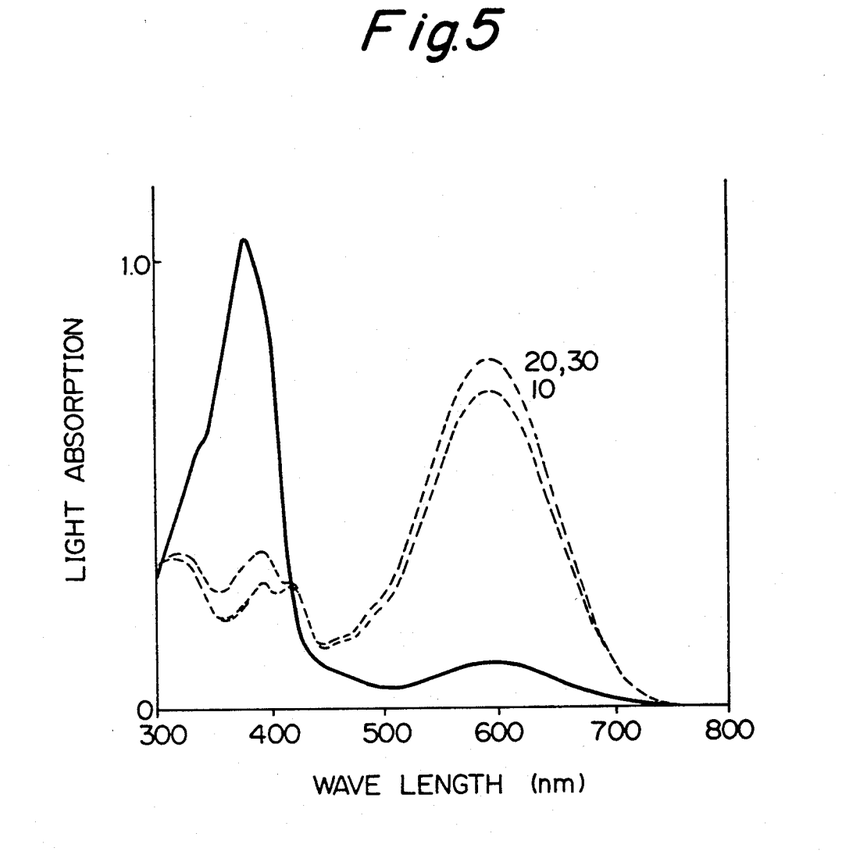
FIG. 5 is absorption spectrum changes for the photochromism of the photochromic compound in Example 4.

The fulgide compound obtained in Example 4 was dissolved in toluene to produce a $2.5 \times 10^{-5}$ mol/l solution which was then subjected light radiation test. The result is shown in FIG. 5 in which figures indicate irradiation time in second.

EXAMPLE 5

Synthesis of (E)-α-2-methyl-5-(1, 3, 3-trimethyl-2-indolylidene) vinyl-3-tienilethylidene (isopropylidene) succinic anhydride.

As a substitute for the middle product in Example 1, i.e. 4-acetyl-5-methyl-2-phenyloxazole, 3-acetyl-2-methyl-5-(1, 3, 3-trimethyl-2-indolylidene) vinyl thiophen was used under conditions same as those in Example 1 to obtain 10 mg of the above-described fulgide compound (melting point; 135° to 140° C.). The result of measurement applied to this compound is shown in Table 5.

TEST 5

Figure 6:
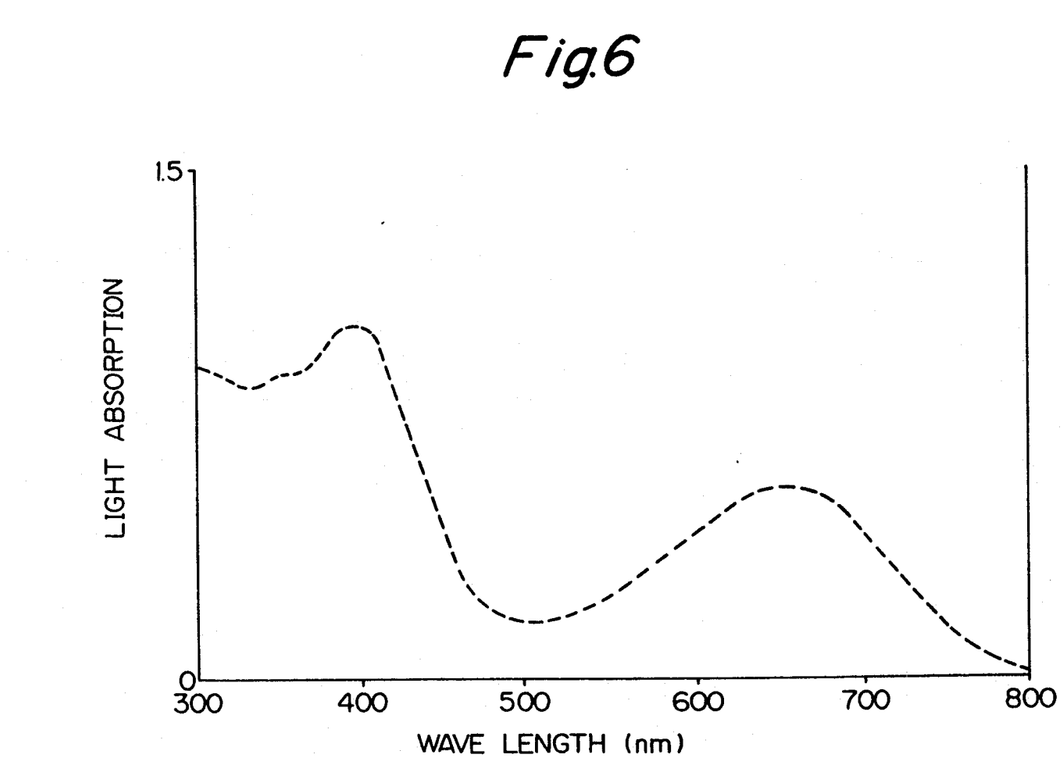
FIG. 6 is a absorption spectrum of the colored from of the photochromic compound in Example 5.

The fulgide compound obtained in Example 5 was dissolved in toluene to obtain $1 \times 10^{-4}$ mol/l solution which was then subjected to light radiation as in Test 2. The resultant absorption spectrum is shown in FIG. 6.

In accordance with the present invention, introduction of electron donative groups into the heteroaromatic structure of a fulgide type photochromic compound assures high long wave length sensitivity without any lowering in its thermal stability, namely maintenance of colored and uncolored form.

TABLE 1

| chemical formula | melting point in °C. | NMR spectrum δ (ppm) solvent CDCl₃ internal standard TMS | | | wave length* in nm |
|---|---|---|---|---|---|
| (structure) | 157 to 160 | 1.40 (3H) | singlet R₄ | methyl | 462 |
| | | 2.13 (3H) | singlet R₅ | methyl | |
| | | 2.37 (3H) | singlet R₂ | methyl | |
| | | 2.73 (3H) | singlet R₃ | methyl | |
| | | 7.37 to 8.07 (5H) | multiplet | phenyl | |

*the maximum absorption wave length at colouration

TABLE 2

| chemical formula | melting point in °C. | NMR spectrum δ (ppm) solvent CDCl₃ internal standard TMS | | | wave length* in nm |
|---|---|---|---|---|---|
| (structure) | 202 to 204 | 1.97 (3H) | singlet (1) | methyl | 510 |
| | | 2.32 (6H) | singlet (2,3) | methyl | |
| | | 2.44 (3H) | singlet (4) | methyl | |
| | | 3.00 (6H) | Singlet N | methyl | |
| | | 6.70 (2H) | doublet | aromatic | |
| | | 7.85 (2H) | doublet | aromatic | |

*the maximum absorption wave length at colouration

TABLE 3

| chemical formula | melting point in °C | NMR spectrum δ (ppm) solvent CDCl₃ internal standard TMS | | | wave length* in nm |
|---|---|---|---|---|---|
|  | 209 to 210 | 2.00 (3H) | singlet (1) | methyl | 530 |
| | | 2.28 (3H) | singlet (2) | methyl | |
| | | 2.30 (3H) | singlet (3) | methyl | |
| | | 2.43 (6H) | singlet (4) | methyl | |
| | | 2.98 (6H) | singlet N | methyl | |
| | | 6.45 to 7.60 (6H) | multiplet | methyl, vinyl | |

*the maximum absorption wave length at colouration

TABLE 4

| chemical formula | melting point in °C | NMR spectrum δ (ppm) solvent CDCl₃ internal standard TMS | | | wave length* in nm |
|---|---|---|---|---|---|
|  | 168 to 172 | 1.15 (6H) | triplet (4) | methyl | 600 |
| | | 1.70 (3H) | singlet (1) | methyl | |
| | | 2.40 (6H) | singlet (2,3) | methyl | |
| | | 3.32 (4H) | qualtet | methylene | |
| | | 6.62 to 7.47 (8H) | multiplet | aromatic, vinyl | |

*the maximum absorption wave length at colouration

We claim:

1. A photochromic compound characterized by a general formula (I)

in which
said $R_1$ to $R_4$ in said formula indicate hydrogen, an alkyl group, or an aryl group,
said X in said formula indicates oxygen or N—$R_6$, $R_6$ indicating hydrogen, an alkyl group, an aryl group, or an allyl group,
said ring A is given in the form of one of the following four chemical groups:

(II)

(V)

-continued

(VI)

(VII)

in said chemical group (II),
$R_5$ is an electron donating group and in the form of an indolyl group, a compound as shown in (VIII):

(VIII)

(in which said $R_{10}$ indicates an alkoxyl group, an amino group, a di-alkyl amino group, or a monoalkyl amino group; and l and m indicate integers 0 to 5), or a compound as shown in (IX):

(IX)

(in which said $R_8$ indicates an alkyl group, an aryl group, an aralkyl group, or an allyl group; said ring B indicates a 5 or 6 membered heteroaromatic ring or a condensed ring containing a 5 or 6 membered heteroaromatic ring; and n indicates an integer from 0 to 4), and in said chemical groups (V) to (VII), $R_5$ is given in the form of an amino group, a di-alkyl amino group, a mono-alkyl amino group, a pyrrolyl group, an indolyl group, a compound as shown in (XII):

(XII)

(in which said $R_{10}$ indicates an alkoxyl group, an amino group, a di-alkyl amino group, a mono-alkyl amino group, 1 indicates an integer from 0 to 5; and m indicates an integer from 1 to 5), or a compound as shown in (XIII):

(XIII)

(in which said $R_8$ indicates an alkyl group, an aryl group, an aralkyl group, or an allyl group; said ring B indicates a 5 or 6 membered heteroaromatic ring or a condensed ring containing a 5 or 6 membered heteroaromatic ring; and n indicates an integer from 0 to 4), and in said chemical groups (V) and (VI), k is 1 or 2, and in said chemical group (VII), k is an integer from 1 to 4; z indicates O, S, N—$R_9$ (in which $R_9$ indicates an alkyl group, an aryl group, an aralkyl group, or an allyl group).

* * * * *